United States Patent [19]
Yamanishi

[11] Patent Number: 5,933,226
[45] Date of Patent: Aug. 3, 1999

[54] ATTACHMENT FOR A CONCENTRATION MEASURING APPARATUS AND A CONCENTRATION MEASURING SYSTEM

[75] Inventor: Akio Yamanishi, Hyogo-Ken, Japan

[73] Assignee: Minolta Co., Ltd., Osaka, Japan

[21] Appl. No.: 08/861,570

[22] Filed: May 22, 1997

[30] Foreign Application Priority Data

May 23, 1996 [JP] Japan ................................. 8-128321

[51] Int. Cl.⁶ .............................. A61B 5/00; G01N 33/48
[52] U.S. Cl. .............................. 356/39; 356/40; 600/310; 600/315
[58] Field of Search ....................... 356/39, 40; 600/310, 600/315, 322

[56] References Cited

U.S. PATENT DOCUMENTS

| | | |
|---|---|---|
| 4,236,826 | 12/1980 | Yamanishi . |
| 4,267,844 | 5/1981 | Yamanishi . |
| 5,259,382 | 11/1993 | Kronberg ................................. 600/315 |
| 5,460,177 | 10/1995 | Purdy et al. .............................. 356/39 |
| 5,567,869 | 10/1996 | Hauch et al. ............................. 356/39 |
| 5,632,273 | 5/1997 | Suzuki ..................................... 356/39 |

Primary Examiner—Robert Kim
Assistant Examiner—Zandra V. Smith
Attorney, Agent, or Firm—Burns, Doane, Swecker & Mathis, LLP

[57] ABSTRACT

An attachment is designed such that a concentration measuring apparatus is attachable to and detachable from it. Inside the leading end portion of the attachment, leading ends of two light guide members are provided opposite to each other so as to hold a micro cuvette mounted on the attachment. One light guide member guides light from a light source of the concentration measuring apparatus to subject matter in the micro cuvette while the other guides light from the subject matter to light receiving elements of the concentration measuring apparatus. The concentration measuring apparatus calculates a concentration of the subject matter based on respective outputs from the light receiving elements.

18 Claims, 5 Drawing Sheets

ATTACHMENT FOR A CONCENTRATION MEASURING APPARATUS AND A CONCENTRATION MEASURING SYSTEM

BACKGROUND OF THE INVENTION

This invention relates to an attachment operable to accommodate a concentration measuring apparatus capable of indirectly measuring a concentration of subject matter in a human body or a plant, e.g., serum bilirubin, oxygen in the blood, blood glucose, chlorophyll, to enable direct measurement of a concentration of subject matter, and also to a concentration measuring system for directly or indirectly measuring a concentration of subject matter.

Generally, icterus, particularly severe icterus of infants may cause a death or, even if a patient can escape from a death, it may progress to nuclear icterus which causes sequelae or aftereffects such as cerebral palsy. Thus, the detection of icterus in an early stage is very crucial.

Accordingly, the icterus of a patient has been diagnosed using a concentration measuring apparatus (icterus detector) disclosed in, e.g., U.S. Pat. No. 4,267,844 without collection of blood sample. This icterus detector includes a light source for irradiating light to the skin of a human body and at least two light receiving elements for receiving light components of the reflected light from the skin in different wavelength ranges which correspond to absorptions by bilirubin pigmented in subcutaneous fat differ. The degree or stage of icterus is measured based on the outputs of the respective light receiving elements. In this way, the degree of icterus is indirectly measured by measuring the concentration of bilirubin pigmented in subcutaneous fat instead of measuring a serum bilirubin concentration.

The above icterus detector is designed to indirectly measure the degree of icterus and is used as a screening apparatus at medical institutions. For an infant supposed to have a high possibility of suffering from icterus as a result of a through-the-skin bilirubin measurement (indirect measurement), his blood is collected and a serum bilirubin concentration is accurately measured by a serum bilirubin concentration measuring apparatus. A final diagnosis is given based on this measurement result. Unlike the icterus detector, the serum bilirubin concentration measuring apparatus directly measures a serum bilirubin concentration by projecting light to the collected blood. This requires the medical institutions treating infants to be equipped with two kinds of apparatuses, increasing a burden for the necessary equipment.

Although there are a plurality of types of serum bilirubin concentration measuring apparatuses, measurement accuracy varies among these apparatuses, presenting a problem of low stability.

Under these circumstances, there have been demands from the medical institutions for an improved icterus detector which can conduct not only a through-the-skin bilirubin measurement but also for a serum bilirubin measurement, and for a concentration measuring system which can selectively conduct direct and indirect measurement of a bilirubin concentration.

Although the above description is limited to the case of measuring a bilirubin concentration, the medical institutions have similar problems and demands for measurements of oxygen in the blood, blood glucose, etc. The above problems and demands have been also found in different fields, e.g., a field of measuring chlorophyll.

SUMMARY OF THE INVENTION

In view of the above problems, it is a first object of the present invention to provide an attachment for use with a concentration measuring apparatus which, by being used together with a concentration measuring apparatus capable of indirectly measuring a concentration of subject matter included in a human body or a plant, enables direct measurement of a concentration of subject matter by the concentration measuring apparatus.

It is a second object of the present invention to provide a concentration measuring system which can accurately or precisely conduct direct and indirect measurement of subject matter included in a human body or a plant.

It should be noted that human bodies and plants are referred to as "object" throughout the specification below.

The present invention is directed to an attachment for use with a concentration measuring apparatus which irradiates light, having a first component of a first wave length and a second component of a second wave length different from the first wave length, from a light source on an object including subject matter to-be-measured and receives the first and second components of light from the object by first and second light receiving elements, respectively, to measure a concentration of the subject matter. The attachment comprises: a body which removably accommodates the concentration measuring apparatus, the body including a test container reception portion which receives a test container containing the subject matter; a first light guider for guiding the light from the light source of the concentration measuring apparatus to the subject matter in the test container; and a second light guider for guiding the light from the subject matter in the test container to the first and second light receiving elements of the concentration measuring apparatus.

The present invention is also directed to a concentration measuring system comprising: (a) a concentration measuring apparatus and (b) an attachment. The concentration measuring apparatus comprises (a-1) a light source for emitting light having a first component of a first wave length and a second component of a second wave length different from the first wave length, (a-2) a first main light guider having first and second ends, the first main light guider receiving the light from the light source through the first end, guiding the light to the second end and emitting the light toward a subject matter side, (a-3) a second main light guider having first and second ends, the second main light guider receiving light from the subject matter side through the first end and guiding the light to the second end, (a-4) first and second light receiving elements for receiving the first and second components of the light from the second end of the second main light guider, respectively, and (a-5) a calculator for calculating a concentration of the subject matter based on respective outputs from the first and second light receiving elements. The attachment comprises (b-1) a body which removably accommodates the concentration measuring apparatus, the body including a test container reception portion which receives a test container containing the subject matter, (b-2) a first auxiliary light guider for guiding the light from the second end of the first main light guider to the subject matter in the test container, and (b-3) a second auxiliary light guider for guiding light from the subject matter in the test container to the first end of the second main light guider.

These and other objects, features and advantages of the present invention will become more apparent upon a reading of the following detailed description and accompanying drawings.

DETAILED DESCRIPTION OF THE PREFERRED EMBODIMENTS OF THE INVENTION

Figure 1:
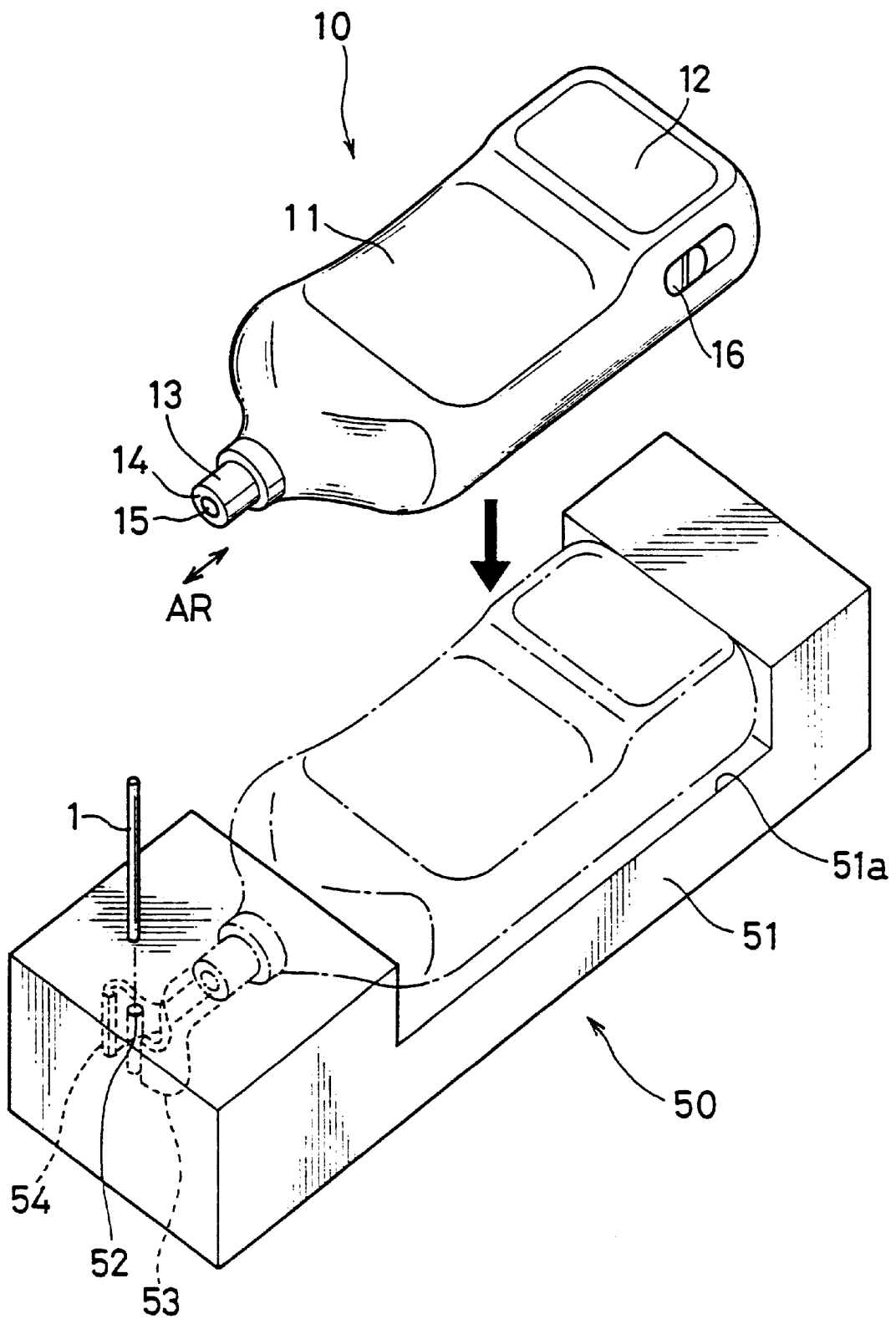
FIG. 1 is a perspective view of a concentration measuring system according to one embodiment of the invention.

FIG. 1 is a perspective view showing a concentration measuring system according to one embodiment of the invention. This system is constructed by a known concentration measuring apparatus 10 and an attachment 50. The following description is made taking an icterus detector for measuring a degree or stage of icterus by measuring a bilirubin concentration as an example.

The concentration measuring apparatus 10 has a casing 11 of such dimensions as to be placed within a palm, and an optical system and electric elements are arranged within this casing 11. Further, a display device 12 for displaying a measurement result (a concentration of bilirubin pigmented in subcutaneous fat and a serum bilirubin concentration) is provided at a rear end of the upper surface of the casing 11. At a leading end of the casing 11, a cylindrical projection 13 is so provided as to be projectable and retractable with respect to the casing 11 as shown by the arrow AR. The projection 13 is biased in a projecting direction (leftward direction of the arrow AR) with respect to the casing 11 by a spring member or like biasing means (not shown). When a measurer presses the projection 13 against a part of an object's body, e.g., his forehead, the projection is pushed into the casing 11 against the biasing force of the biasing means to cause a xenon tube (light source) to emit light. The light source is to be described later. Upon irradiation of the xenon tube, white light from the xenon tube comes out of an outer peripheral portion 14 of an end face of the projection 13 and is incident on the skin of the body. The reflected light is incident on the optical system inside the casing 11 through a center portion 15 of the end face of the projection 13. Further, a power switch 16 is provided at a rear end of one side surface of the casing 11 and a reset switch (not shown) is provided at the opposite side surface.

The attachment 50 is designed such that the concentration measuring apparatus 10 is attachable to and detachable from it. Specifically, in a center portion of the upper surface of a main body 51 of the attachment 50, a recess 51a is so formed as to conform to the outer shape of the concentration measuring apparatus 10. The recess 51a serves as a mount portion for accommodating the concentration measuring apparatus 10. When the concentration measuring apparatus 10 is mounted in the recess 51a, the concentration measuring apparatus 10 and the attachment 50 construct a single unit and the projection 13 is pushed into the casing 11 against the biasing force of the biasing means to cause the xenon tube to irradiate. Further, a vertically extending opening 52 is formed at a leading end portion of the upper surface of the attachment 50. A micro cuvette (capillary glass tube) 1 containing blood collected from the object is mounted on the attachment 50 by being inserted into the opening 52. Accordingly, the opening 52 serves as a test container reception portion of the attachment 50. In this embodiment, the micro cuvette 1 is used as a test container for the blood containing bilirubin, i.e., subject matter. According to the invention, however, other containers may be used as a test container.

Inside the leading end portion of the attachment 50, the leading ends of two light guide members 53, 54 are provided opposite to each other so as to hold the micro cuvette 1 mounted on the attachment 50 as indicated by dotted lines in FIG. 1. When the concentration measuring apparatus 10 is mounted in the attachment 50 as described above, the rear ends of the light guide members 53, 54 are spaced apart from the peripheral portion 14 and the center portion 15 of the end face of the projection 13 by a specified distance, thereby defining a wave path. Accordingly, when the concentration measuring apparatus 10 is mounted in the attachment 50 after the micro cuvette 1 is mounted in the attachment 50, the xenon tube emits light as described above to project it onto the blood in the micro cuvette 1 via the peripheral portion 14 and the light guide member 53. The light passed through the blood is guided to a light receiving element via the light guide member 54 and the center portion 15. The light receiving element is to be described later.

Figure 2:
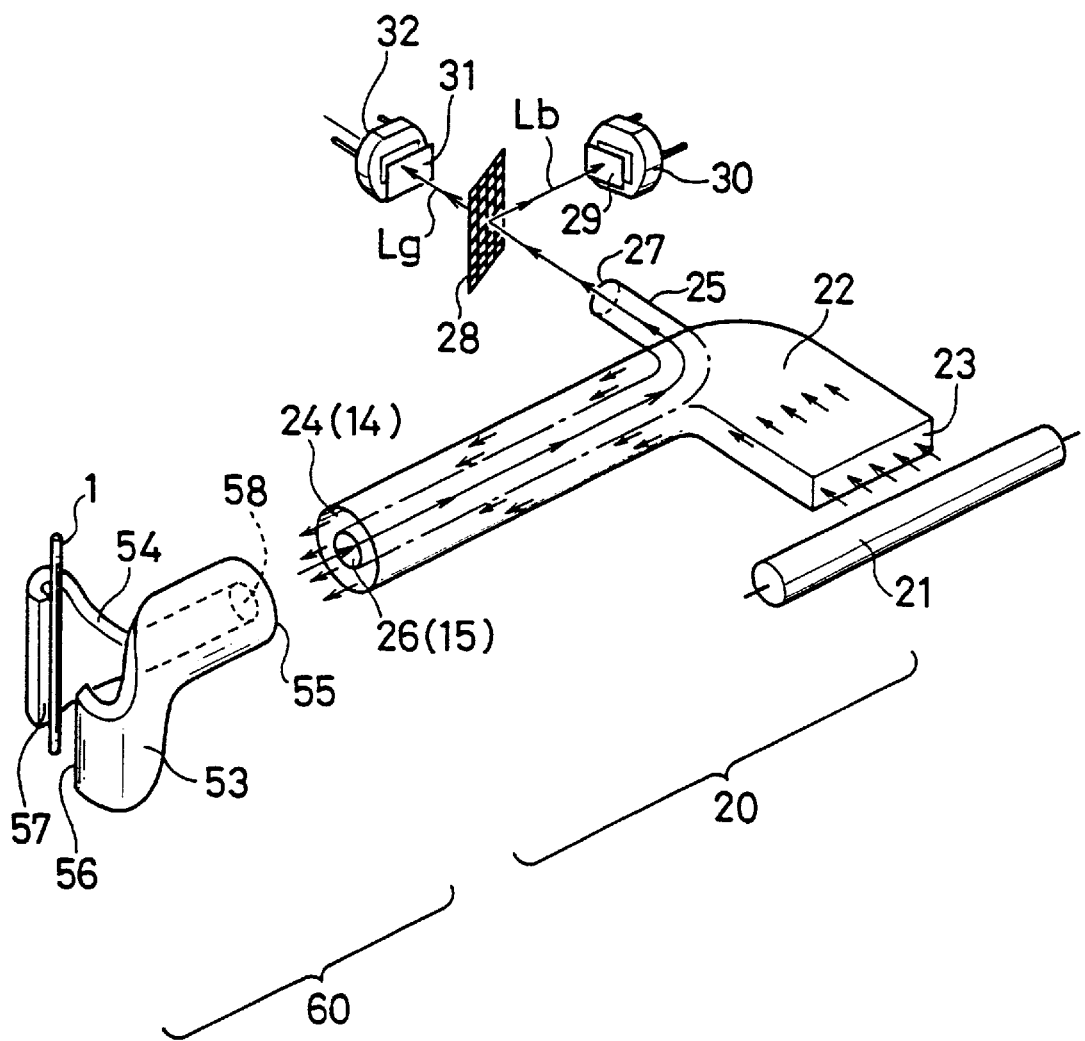
FIG. 2 is an exploded perspective view of the concentration measuring system.

FIG. 2 is a perspective view showing optical systems of the concentration measuring system of FIG. 1. In FIG. 2, indicated at 20 is an optical system of the concentration measuring apparatus 10 and at 60 is an optical system of the attachment 50.

The optical system 20 of the measuring apparatus 10 includes a xenon tube 21 which acts as a light source. When this xenon tube 21 is fired, light (white light) having a plurality of wavelengths is generated. One end 23 of a glass fiber 22 which acts as a first main light guiding means is so provided as to face the xenon tube 21. The light from the xenon tube 21 is guided to an other end 24 (corresponding to the peripheral portion 14 of the end face of the projection 13) of the glass fiber 22 and comes therefrom. The propagation of the light partly differs depending upon a case where the concentration of bilirubin pigmented in subcutaneous fat is measured by pressing the concentration measuring apparatus 10 against a part of the body of an object (through-the-skin bilirubin measurement: indirect measurement) and a case where a serum bilirubin concentration is measured by attaching the concentration measuring apparatus 10 to the attachment 50 (serum bilirubin measurement: direct measurement). Accordingly, the two cases are separately described below.

In the case of the through-the-skin bilirubin measurement (indirect measurement), the light from the other end 24 of the glass fiber 22 is incident on the skin of the object; the scattered light from the skin surface having components thereof in a blue light wavelength range strongly absorbed by bilirubin pigmented in subcutaneous fat is incident on one end 26 (corresponding to the center portion 15 of the end face of the projection 13) of a glass fiber 25 which acts as a second main light guiding means; is guided to an other end 27 of the glass fiber 25; and comes out of the other end 27. This light is incident on a dichroic mirror 28 and is split into a light component Lb of blue wavelengths and a light component Lg of green wavelengths. The light component Lb is received by a light receiving element 30 via a blue filter 29, whereas the light component Lg is received by a light receiving element 32 via a green filter 31.

On the other hand, in the case of the serum bilirubin measurement (direct measurement), the concentration measuring apparatus 10 is attached to the attachment 50. As described above, one end (rear end) 55 of the light guide member 53 which acts as a first auxiliary light guiding means faces the other end 24 of the glass fiber 22 as the first main light guiding means. The light from the glass fiber 22 is incident on the light guide member 53 via the one end 55; propagates in the light guide member 53; and is projected onto the blood in the micro cuvette 1 from an other end (leading end) 56 of the light guide member 53. The light having passed through the blood is incident on the light guide member 54 via one end (leading end) 57 of the light guide member 54 which acts as a second auxiliary light guiding means, and is incident on the one end 26 (corresponding to the center portion 15 of the end face of the projection 13) of the glass fiber 25 as the second main light guiding means via the other end 58 after being guided to the other end 58.

Figure 3:
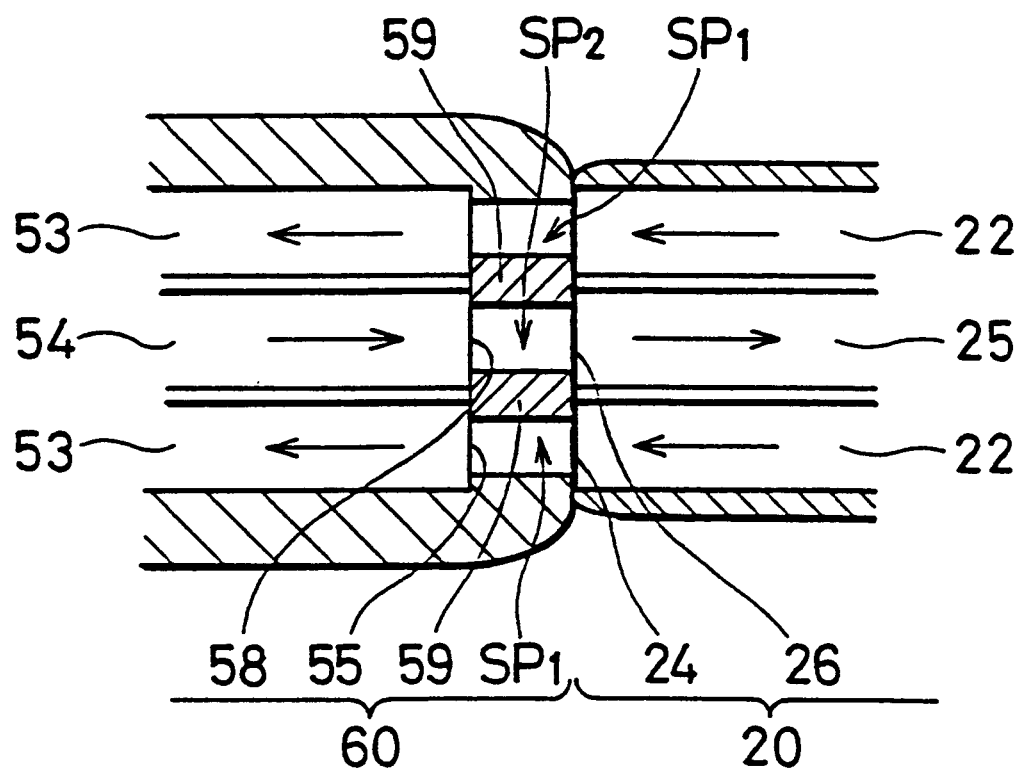
FIG. 3 is an enlarged sectional view of a connection portion of optical systems of the concentration measuring system.

In this embodiment, particularly as shown in FIG. 3, the optical system 20 of the concentration measuring apparatus 10 and the optical system 60 of the attachment 50 are connected via a spacer 59. Between the other end 24 of the glass fiber 22 and the one end 55 of the light guide member 53, there is defined a space SP1 having a thickness equal to that of the spacer 59. Further, between the one end 26 of the glass fiber 25 and the other end 58 of the light guide member 54, there is defined a space SP2 having a thickness equal to that of the spacer 59. Thus, even if the glass fiber 22 and the light guide member 53 are displaced with respect to each other, the light can uniformly be guided from the glass fiber 22 to the light guide member 53 by a diffusion effect in the spaces SP1, SP2. The same can be said for the glass fiber 25 and the light guide member 54. As a result, the influence of the angular dependency of the wavelength characteristic of the dichroic mirror 28 can be prevented.

Referring back to FIG. 2, the light having been incident on the glass fiber 25 is guided to the dichroic mirror 28 by the glass fiber 25 similar to the case of the through-the-skin bilirubin measurement; is split into a light component Lb of blue wavelengths which is then received by the light receiving element 30 via the blue filter 29 and a light component Lg of green wavelengths which is then received by the light receiving element 32 via the green filter 31.

Figure 4:
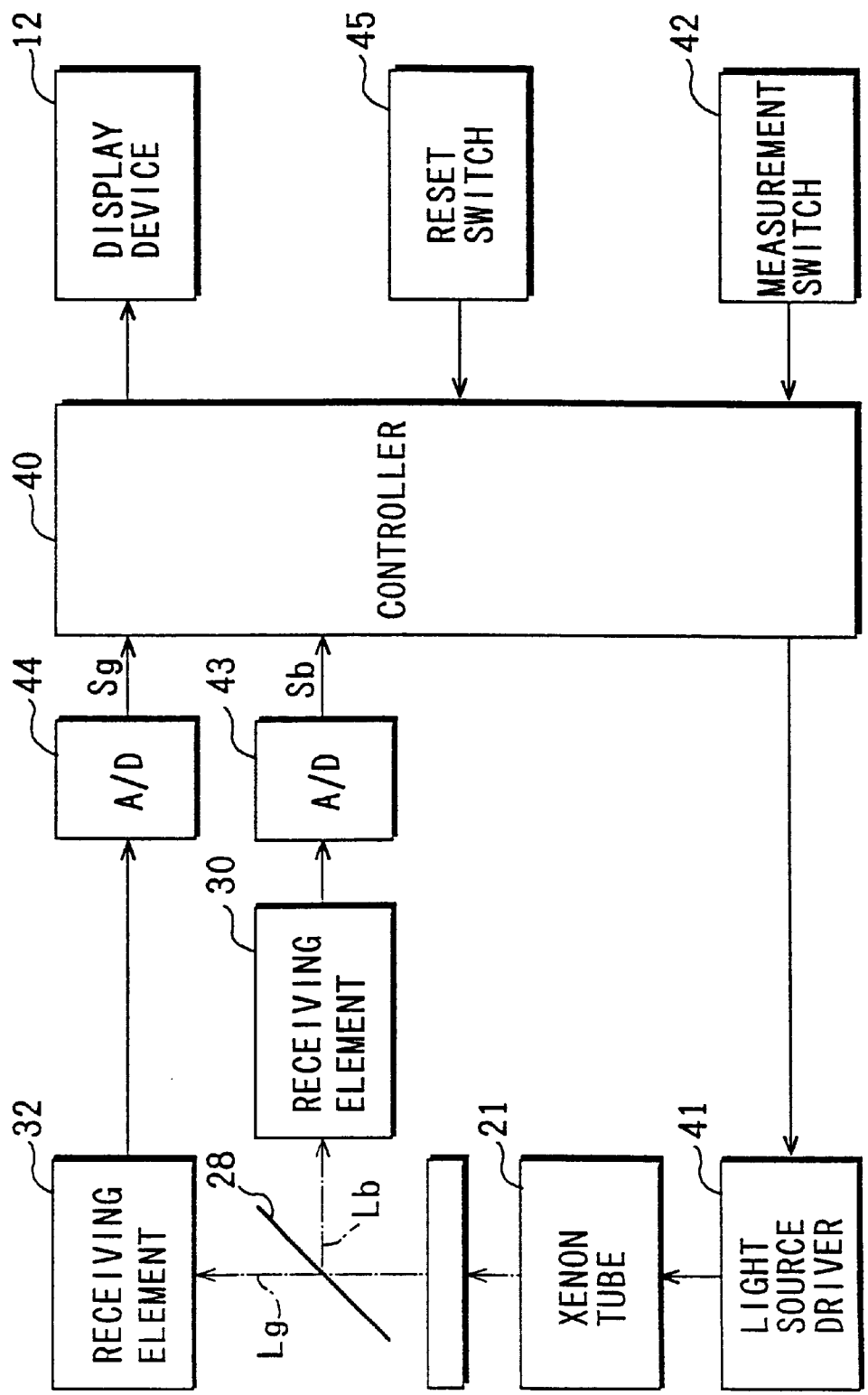
FIG. 4 is a block diagram showing an electrical construction of the concentration measuring apparatus of FIG. 1.

FIG. 4 is a block diagram showing an electrical construction of the concentration measuring apparatus 10 of FIG. 1. The concentration measuring apparatus 10 is provided with a controller 40 for controlling the entire apparatus. The controller 40 is electrically connected with a light source driver 41. When the projection 13 is pressed into the casing 11 against the biasing force of the biasing means as described above, a measurement switch 42 is automatically turned on. In response thereto, the controller 40 gives an emission command signal to the light source driver 41, which causes the xenon tube 21 to emit light. The light receiving elements 30, 32 for receiving the light components Lb, Lg split by the dichroic mirror 28 are electrically connected with the controller 40 via analog-to-digital (A/D) converters 43, 44. Signals Sb, Sg are outputted from the light receiving elements 30, 32 to the controller 40. The controller 40 calculates a bilirubin concentration in accordance with a known principle (e.g., a measurement principle disclosed in U.S. Pat. No. 4,267,844) based on the output signals Sb, Sg. This calculation result is displayed in the display device 12. In FIG. 4, indicated at 45 is a reset switch for clearing the measurement result to reset the concentration measuring apparatus 10 for a next measurement.

Next, the through-the-skin bilirubin measurement and the serum bilirubin measurement by the concentration measuring system as constructed above are described.

In the case of conducting the through-the-skin bilirubin measurement (indirect measurement), the concentration measuring apparatus 10 is solely used without the attachment 50 in the same manner as the prior art to measure the concentration of bilirubin pigmented in the subcutaneous fat of an object. More specifically, after turning on the power switch 16 provided at the front side surface of the casing 11, the measurer presses the reset switch 45 to enable a measurement. The measurer presses the projection 13 of the measuring apparatus 10 against a part of the object, e.g., his forehead. This causes the projection 13 to retract into the casing 11 against the biasing force of the biasing means. When the projection 13 is retracted by a specified amount, the measurement switch 42 is automatically turned on, causing the xenon tube 21 to emit light. The white light from the xenon tube 21 is projected onto the skin of the object, and the light reflected by the object is split by the dichroic mirror 28 into light components of two colors, which are received by the light receiving elements 30, 32, respectively. Then, the controller 40 calculates the concentration of bilirubin pigmented in subcutaneous fat in accordance with the signals Sb, Sg outputted from the light receiving elements 30, 32. This calculation result is displayed in the display device 12.

On the other hand, in the case of conducting a serum bilirubin measurement (direct measurement), a measurer collects blood from an object; puts it into a micro cuvette 1; sets the micro cuvette 1 in the attachment 50; turns on the power switch 16 provided at the front side surface of the casing 11 of the concentration measuring apparatus 10; and presses the reset switch 45 to set a measurement enabling state. When the measuring apparatus 10 is set in the recess 51a of the attachment 50, the measurement switch 42 is automatically turned on, causing the xenon tube 21 to emit light. The white light from the xenon tube 21 is projected onto the micro cuvette 1 via the glass fiber (first main light guiding means) 22 and the light guide member (first auxiliary light guiding means) 53. The light having passed through the micro cuvette 1 is incident on the dichroic mirror 28 via the light guide member (second auxiliary light guiding means) 54 and the glass fiber (second auxiliary light guiding means) 25. The incident light is split into two light components of different colors, which are received by the light receiving elements 30, 32, respectively. The controller 40 calculates a serum bilirubin concentration in the micro cuvette 1 in accordance with the signals Sb, Sg outputted from the light receiving elements 30, 32, and the measurement result is displayed in the display device 12.

In the concentration measuring system according to this embodiment, the serum bilirubin concentration is calculated in the same manner as in the case of the through-the-skin bilirubin measurement, i.e., is calculated in accordance with a program pre-installed in the concentration measuring apparatus 10. Accordingly, the measurement result displayed in the display device 12 during the serum bilirubin measurement needs to be corrected. Such a correction may be made as follows. A comparison table is prepared by conducting measurements for standard samples. The measurer corrects the measurement result with reference to this comparison table.

As described above, according to this embodiment, the concentration of serum bilirubin within the micro cuvette 1 can directly be measured by preparing the attachment 50 and attaching the concentration measuring apparatus 10 to the attachment 50. Accordingly, the concentration measuring apparatus 10 which has conventionally been used as a screening apparatus prior to a serum bilirubin measurement can be used not only for the through-the-skin bilirubin measurement but also for the serum bilirubin measurement.

This leads to a reduced burden on the provision of necessary equipment at medical institutions. Further, since a bilirubin concentration is measured using the same concentration measuring apparatus 10, a measurement accuracy variation among different types of measuring apparatuses which has been a problem with the prior art can be eliminated, with the result that a bilirubin concentration can stably be measured.

Figure 5:
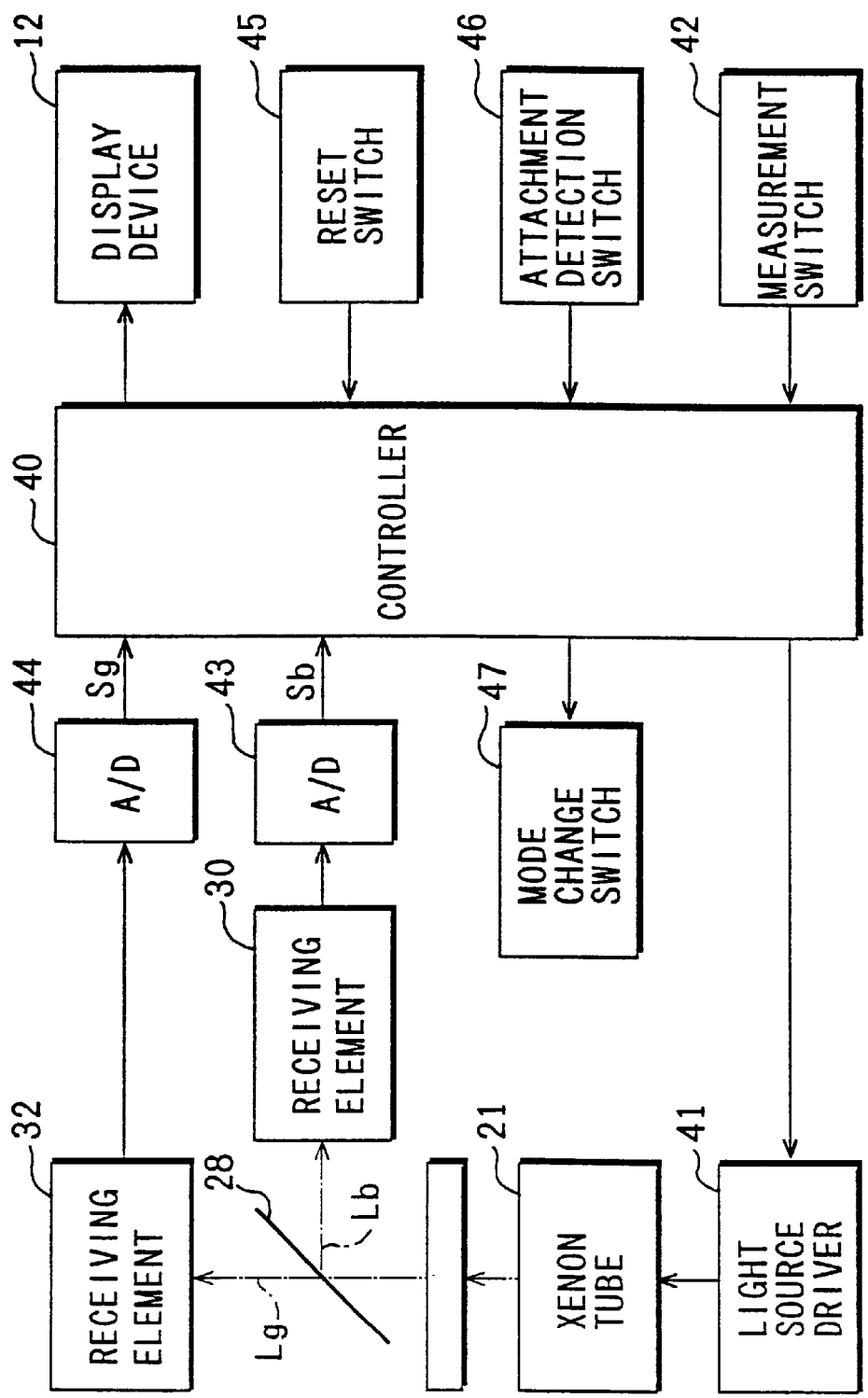
FIG. 5 is a block diagram showing an electrical construction of a concentration measuring system according to another embodiment of the invention.

FIG. 5 is a block diagram showing an electrical construction of a concentration measuring system according to another embodiment of the invention. This concentration measuring system is identical to the aforementioned one except:

(1) The concentration measuring apparatus 10 is additionally provided with an attachment detection switch 46 for detecting whether or not the concentration measuring apparatus 10 is attached to the attachment 50;

(2) A calculation program for the through-the-skin bilirubin measurement and a calculation program for the serum bilirubin measurement are stored in advance in the controller 40. Whether or not the concentration measuring apparatus 10 is attached to the attachment 50 is detected by the switch 46. If the concentration measuring apparatus 10 is not attached to the attachment 50, a bilirubin concentration is calculated based on the signals Sb, Sg in accordance with the calculation program for the through-the-skin bilirubin measurement. On the other hand, if the concentration measuring apparatus 10 is attached to the attachment 50, a bilirubin concentration is calculated based on the signals Sb, Sg in accordance with the calculation program for the serum bilirubin measurement; and (3) The controller 40 sends a mode change signal to a mode change switch 47 based on the state of the attachment detection switch 46 to switchingly set an inoperable state and an operable state in a charging mode.

In the concentration measuring system according to this embodiment, whether or not the concentration measuring apparatus 10 is attached to the attachment 50 is detected and the calculation program is switched based thereon. Thus, a proper and accurate measurement result is constantly displayed in the display device 12 and the use of the comparison table is not necessary.

Although the results of the through-the-skin bilirubin measurement and of the serum bilirubin measurement are both displayed in the display device 12 of the concentration measuring apparatus 10 in this embodiment, a display device may be provided at the attachment 50 and a display may be switchingly made on the two display devices based on whether or not the concentration measuring apparatus 10 is attached to the attachment 50.

In the foregoing embodiments, when the concentration measuring apparatus 10 is attached to the attachment 50, the measurement switch 42 is automatically turned on to measure a serum bilirubin concentration. However, a measurement switch exclusively for the use of the serum bilirubin measurement for controlling the serum bilirubin measurement may be additionally provided at the concentration measuring apparatus 10. With this arrangement, the serum bilirubin concentration can continuously be measured by exchanging the micro cuvettes 1 while the concentration measuring apparatus 10 being attached to the attachment 50 and pressing this exclusive serum bilirubin measurement switch. Instead of providing the exclusive serum bilirubin measurement switch, the reset switch 45 may act also as a serum bilirubin measurement switch only when the concentration measuring apparatus 10 is attached to the attachment 50 (during the serum bilirubin measurement).

The concentration measuring system may also be provided with a calibration function: a standard reagent is measured prior to an actual measurement and a variety of settings are changed and determined so that the measurement result of the standard reagent agrees with a rated value of the standard reagent. By additionally having this calibration function, the between-lot variation of the micro cuvettes 1 used for the serum bilirubin measurement can be corrected.

In the above description, the end face of the projection 13 has a concentric configuration as shown in FIG. 1 and the peripheral portion 14 acts as a light projecting portion while the center portion 15 acts as a light receiving portion. However, the functions of the peripheral portion 14 and the center portion 15 may be reversed. Instead of having a concentric configuration, the end face may be divided into semicircular configurations which act as a light projecting portion and a light receiving portion, respectively.

Although the through-the-skin bilirubin measurement is made using reflected light from the object, light having passed through the object may be used. Further, although the serum bilirubin measurement is made using light having passed through the blood in the micro cuvette 1, the light reflected by the micro cuvette 1 may be used. As a method for obtaining reflected light, the blood collected from the object may be soaked into a filter paper (test container) and the light from the xenon tube 21 is projected onto the filter paper.

In the above description, the concentration measuring apparatus 10 is described taking an icterus detector for measuring the degree of icterus by measuring a bilirubin concentration as an example. However, the concentration measuring apparatus 10 may be a measuring apparatus for indirectly measuring subject matter such as oxygen in the blood, a blood glucose value and chlorophyll.

As described above, the concentration measuring apparatus capable of indirectly measuring subject matter is so constructed as to be detachably attachable to the attachment. When a test container containing the subject matter is set in the main body of the attachment and the measuring apparatus is activated by being attached to the attachment, the light from a light source (light having first and second wavelengths different from each other) is incident on the subject matter via the first auxiliary light guiding means and the light from the subject matter is guided to the first and second light receiving elements via the second auxiliary light guiding means. The light component having the first wavelength is received by the first light receiving element, whereas the light component having the second wavelength is received by the second light receiving element. The concentration of the subject matter is calculated based on the outputs of the first and second light receiving elements. Thus, the concentration of the subject matter can directly be measured by attaching the concentration measuring apparatus to the attachment.

Further, the concentration measuring apparatus may also be constructed such that a light component having the first wavelength and a light component having the second wavelength are projected from the light source onto the subject matter; these light components from the subject matter are received by the first and second light receiving elements; and the concentration of the subject matter is measured based on the outputs of the respective light receiving elements. Accordingly, the concentration of the subject matter can indirectly be measured by solely activating the measuring apparatus, i.e., by projecting the light from the light source onto the surface of a body containing the subject matter. Further, when the sample containing the subject matter is set in the main body of the attachment and the measuring apparatus is activated by being attached to the attachment, the light from the light source is directly projected onto the subject matter to directly measure the concentration of this subject matter. Thus, according to this concentration measuring system, the subject matter can both directly and indirectly be measured by the same system.

Furthermore, if the calculation program is switched based on whether or not the measuring apparatus is attached to the main body of the attachment, the concentration of the subject matter can be measured with high accuracy.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. A concentration measuring system comprising:
   (a) a concentration measuring apparatus comprising
       (a-1) a light source for emitting light having a first component of a first wave length and a second component of a second wave length different from the first wave length,
       (a-2) a first main light guider having first and second ends, said first main light guider receiving the light from said light source through said first end, guiding the light to said second end and emitting the light toward a subject matter side,
       (a-3) a second main light guider having first and second ends, said second main light guider receiving light from the subject matter side through said first end and guiding the light to said second end,
       (a-4) first and second light receiving elements for receiving the first and second components of the light from said second end of said second main light guider, respectively, and
       (a-5) a calculator for calculating a concentration of the subject matter based on respective outputs from said first and second light receiving elements; and
   (b) an attachment comprising
       (b-1) a body which removably accommodates said concentration measuring apparatus, said body including a test container reception portion which receives a test container containing the subject matter,
       (b-2) a first auxiliary light guider for guiding the light from said second end of said first main light guider to the subject matter in said test container, and
       (b-3) a second auxiliary light guider for guiding light from the subject matter in said test container to said first end of said second main light guider.

2. A concentration measuring system as defined in claim 1, further comprising a spacer for defining a space between the subject matter side ends of said first and second main light guiders and the concentration measuring apparatus side ends of said first and second auxiliary light guiders when said concentration measuring apparatus is attached onto said attachment.

3. A concentration measuring system as defined in claim 1, further comprising attachment detector for detecting whether or not said concentration measuring apparatus is attached onto said attachment,
   and wherein said calculator has two different calculating programs and calculates a concentration of the subject matter on the basis of one of the calculating programs in response to the result detected by said attachment detector.

4. A concentration measuring system as defined in claim 3, wherein said concentration measuring apparatus is an icterus detector, and wherein the subject matter is bilirubin.

5. A concentration measuring system as defined in claim 4, wherein said test container is a micro cuvette containing blood collected from a human body to be measured.

6. A concentration measuring system comprising:
   an icterus detector for irradiating light onto the skin of a human body to-be-measured and indirectly measuring a concentration of the bilirubin pigmented in subcutaneous fat of the human body on the basis of light reflected from the skin; and
   an adapter attachment which removably accommodates the icterus detector, said adapter attachment comprising an optical system which guides light from said icterus detector to a test container containing a blood collected from the human body and guides light passed through said test container to said icterus detector when said icterus detector is attached onto said adapter attachment, so that a concentration of the bilirubin in the blood is directly measured by said icterus detector.

7. A concentration measuring system as defined in claim 6, wherein said attachment includes a test container reception portion which receives said test container.

8. A concentration measuring system as defined in claim 7, wherein said test container is a micro cuvette containing blood collected from said human body.

9. A concentration measuring system as defined in claim 6, wherein said icterus detector comprises a controller which changes program for calculating the concentration in response to whether or not said icterus detector is attached to said attachment.

10. A concentration measuring system as defined in claim 9, further comprising attachment detector for detecting whether or not said icterus detector is attached to said attachment,
    and wherein said controller changes the program in response to the result detected by said attachment detector.

11. A concentration measuring system as defined in claim 6, further comprising a display device for displaying a measurement result.

12. A concentration measuring system as defined in claim 11, wherein said display device is proved on said icterus detector.

13. An attachment apparatus capable of removably receiving an icterus detector for irradiating light onto the skin of a human body to-be-measured and indirectly measuring a concentration of the bilirubin pigmented in subcutaneous fat of the human body on the basis of the light reflected from the skin, said attachment apparatus comprising:
    a body portion adapted for removably receiving said icterus detector; and
    an optical system which guides light from said icterus detector to a test container containing a blood collected from the human body and guides light passed through said test container to said icterus detector when said icterus detector is attached onto said attachment, for directly measuring a concentration of the bilirubin in the blood with said icterus detector.

14. An attachment as defined in claim 13, wherein said attachment includes a test container reception portion which receives said test container.

15. An attachment as defined in claim 14, wherein said test container is a micro cuvette containing blood collected from said human body.

16. In a concentration measuring apparatus including a light source, a first light guide member, a second light guide member, a first light receiving element, and a second light receiving element, the measuring apparatus indirectly measuring a concentration of a subject matter within an object based upon respective outputs from the first and light receiving elements, the improvement comprising:

an adapter enabling a direct measurement of the concentration of the subject matter, said adapter including:

a body adapted for removable attachment of the indirect concentration measuring apparatus, said body having a test container reception portion for receiving a test container containing the subject matter;

a first adapter light guide member for guiding light from the light source of the concentration measuring apparatus to the subject matter contained within the test container; and a second adapter light guide member for guiding light from the subject matter in said test container to the first and second light receiving elements of the concentration measuring apparatus, to thereby directly measure the concentration of the subject matter in said test container.

17. The measuring apparatus as defined in claim 16, wherein said indirect concentration measuring apparatus is an icterus detector, and wherein the subject matter is bilirubin.

18. The measuring apparatus as defined in claim 17, wherein said test container is a micro cuvette containing blood collected from a human body to be measured.

* * * * *